United States Patent [19]

Bommannan et al.

[11] Patent Number: 5,323,769
[45] Date of Patent: Jun. 28, 1994

[54] ULTRASOUND-ENHANCED DELIVERY OF MATERIALS INTO AND THROUGH THE SKIN

[75] Inventors: Durairaj Bommannan; Hirohisa Okuyama; Richard H. Guy, all of San Francisco; Paul Stauffer, San Rafael, all of Calif.; Gordon L. Flynn, Ann Arbor, Mich.

[73] Assignees: Cygnus Therapeutic Systems, Redwood City; The Regents of the University of California, Oakland, both of Calif.

[21] Appl. No.: 101,491

[22] Filed: Aug. 2, 1993

Related U.S. Application Data

[62] Division of Ser. No. 844,732, Mar. 2, 1992, Pat. No. 5,231,975, which is a division of Ser. No. 484,560, Feb. 23, 1990, Pat. No. 5,115,805.

[51] Int. Cl.$^5$ .................. A61B 17/00; A16M 37/00
[52] U.S. Cl. .................................. 601/2; 604/20
[58] Field of Search .............. 128/24 AA, 660.03; 604/20, 22

[56] References Cited

U.S. PATENT DOCUMENTS

| | | |
|---|---|---|
| 4,372,296 | 2/1983 | Fahim . |
| 4,692,139 | 9/1987 | Stiles . |
| 4,767,402 | 8/1988 | Kost et al. . |
| 4,780,212 | 10/1988 | Kost et al. . |
| 4,787,888 | 11/1988 | Fox ................................ 128/24 AA |
| 4,791,915 | 12/1988 | Barsotti et al. . |
| 4,804,364 | 2/1989 | Dieras . |
| 4,821,740 | 4/1989 | Tachibana et al. . |
| 4,953,565 | 9/1990 | Tachibana et al. . |
| 5,016,615 | 5/1991 | Driller et al. ...................... 604/20 |
| 5,115,805 | 5/1992 | Bommannan et al. . |
| 5,231,975 | 8/1993 | Bommannan et al. ........ 128/24 AA |

FOREIGN PATENT DOCUMENTS

| | | |
|---|---|---|
| 3736072 | 4/1989 | Fed. Rep. of Germany ........ 604/20 |
| 8906989 | 8/1989 | PCT Int'l Appl. .................... 604/20 |
| 0770496 | 10/1980 | U.S.S.R. . |
| 0799750 | 1/1981 | U.S.S.R. . |
| 0878268 | 11/1981 | U.S.S.R. . |
| 884700 | 11/1981 | U.S.S.R. . |
| 1111759 | 9/1984 | U.S.S.R. . |
| 1153917 | 5/1985 | U.S.S.R. . |
| 1181664 | 9/1986 | U.S.S.R. . |

OTHER PUBLICATIONS

Benson, H. et al., "Use of ultrasound to enhance percutaneous absorption of benzydamine" *Physical Therapy* (1989) 69(2):113-118.

Escoffier, C. et al., "In vitro study of the velocity of ultrasound in the skin" *Bioeng. Skin* (1986) 2:87-94.

Griffin, J. E. et al., "Ultrasonic movement of cortisol into pig tissue" *Amer. J. Phys. Medicine* (1965) 44(1):20-25.

Griffin, J. E. et al., "Physiological effects of ultrasonic energy as it is used clinically" *J. Amer. Phys. Therapy Assoc.* (1966) 46:18-26.

Griffin, J. E. et al., "Patients treated with ultrasonic driven hydrocortisone and with ultrasound alone" *Phys. Therapy* (1967) 47(7):594-601.

Griffin, J. E. et al., "Low-intensity phonophoresis of cortisol in swine" *Phys. Therapy* (1968) 48(12):1336-1344.

Griffin, J. E. et al., "Effect of ultrasonic frequency on phonophoresis of cortisol into swine tissues" *Amer. J. Phys. Medicine* (1972) 51(2):62-72.

Kost, J. et al., "Effect of therapeutic ultrasound on skin permeability" *Proceed. Intern. Symp. Control. Rel. Bioact. Mater.* (1989) 16(141):294-295.

(List continued on next page.)

*Primary Examiner*—Lee S. Cohan
*Assistant Examiner*—K. M. Pfaffle
*Attorney, Agent, or Firm*—Morrison & Foerster

[57] ABSTRACT

A method for enhancing the permeability of the skin or other biological membrane to a material such as a drug is disclosed. In the method, the drug is delivered in conjunction with ultrasound having a frequency of above about 10 MHz. The method may also be used in conjunction with chemical permeation enhancers and/or with iontophoresis.

21 Claims, 11 Drawing Sheets

OTHER PUBLICATIONS

Lutz, H. et al., *Manual of Ultrasound: Basic Physical and Technical Principles* (1984) (Berlin:Springer-Verlag) Chapter 1.

McElnay, J. E., "The influence of ultrasound on the percutaneous absorption of fluocinolone acetonide" *Int. J. Pharmaceutics* (1987) 40:105–110.

Miyasaki, S. et al., "External control of drug release: controlled release of insulin from a hydrophilic polymer by ultrasound irradiation in diabetic rats" *J. Pharm. Pharmacol.* (1988) 40:716–717.

Novak, E., "Experimental transmission of lidocaine through intact skin by ultrasound" *Arch. Phys. Medicine & Rehab.* (1964) 45:231–232.

Skauen, D. M. et al., "Phonophoresis" *Int. J. Pharmaceutics* (1984) 20:235–245.

Tyle, P. et al., "Drug delivery by phonophroesis" *Pharmaceutical Research* (1989) 6(5):355–361.

ULTRASOUND-ENHANCED DELIVERY OF MATERIALS INTO AND THROUGH THE SKIN

This application is a division of application Ser. No. 07/844,732 filed Mar. 2, 1992, now U.S. Pat. No. 5,231,975 which is a divisional of application Ser. No. 07/484,560, now U.S. Pat. No. 5,115,805, filed Feb. 23, 1990.

TECHNICAL FIELD

This invention relates generally to the field of drug delivery. More particularly, the invention relates to a method of enhancing the rate of permeation of topically, transmucosally or transdermally applied materials using high frequency ultrasound.

BACKGROUND

The delivery of drugs through the skin ("transdermal drug delivery" or "TDD") provides many advantages; primarily, such a means of delivery is a comfortable, convenient and non-invasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively impermeable membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the stratum corneum, a layer approximately 5-15 micrometers thick over most of the body, which presents the primary barrier to absorption of topical compositions or transdermally administered drugs. It is believed to be the high degree of keratinization within its cells as well as their dense packing and cementation by ordered, semicrystalline lipids which create in many cases a substantially impermeable barrier to drug penetration. Applicability of transdermal drug delivery is thus presently limited, because the skin is such an excellent barrier to the ingress of topically applied materials. For example, many of the new peptides and proteins now produced as a result of the biotechnology revolution cannot be delivered across the skin in sufficient quantities due to their naturally low rates of skin permeability.

Various methods have been used to increase skin permeability, and in particular to increase the permeability of the stratum corneum (i.e., so as to achieve enhanced penetration, through the skin, of the drug to be administered transdermally). The primary focus has been on the use of chemical enhancers, i.e., wherein drug is coadministered with a penetration enhancing agent (or "permeation enhancer"). While such compounds are effective in increasing the rate at which drug is delivered through the skin, there are drawbacks with many permeation enhancers which limit their use. For example, many permeation enhancers are associated with deleterious effects on the skin (e.g., irritation). In addition, control of drug delivery with chemical enhancement can be quite difficult.

Iontophoresis has also been used to increase the permeability of skin to drugs, and involves (1) the application of an external electric field, and (2) topical delivery of an ionized form of drug (or of a neutral drug carried with the water flux associated with ion transport, i.e., via "electroosmosis"). While permeation enhancement via iontophoresis has, as with chemical enhancers, been effective, there are problems with control of drug delivery and the degree of irreversible skin damage induced by the transmembrane passage of current.

The presently disclosed and claimed method involves the use of ultrasound to decrease the barrier function of the stratum corneum and thus increase the rate at which a drug may be delivered through the skin. "Ultrasound" is defined as mechanical pressure waves with frequencies above 20,000 Hz (see, e.g., H. Lutz et al., *Manual of Ultrasound: 1. Basic Physical and Technical Principles* (Berlin: Springer-Verlag, 1984)).

As discussed by P. Tyle et al. in *Pharmaceutical Research* 6(5):355-361 (1989), drug penetration achieved via "sonophoresis" (the movement of drugs through skin under the influence of an ultrasonic perturbation; see D. M. Skauen and G. M. Zentner, *Int. J. Pharmaceutics* 20:235-245 (1984)), is believed to result from thermal, mechanical and chemical alteration of biological tissues by the applied ultrasonic waves. Unlike iontophoresis, the risk of skin damage appears to be low.

Applications of ultrasound to drug delivery have been discussed in the literature. See, for example: P. Tyle et al., supra (which provides an overview of sonophoresis); S. Miyazaki et al., *J. Pharm. Pharmacol.* 40:716-717 (1988) (controlled release of insulin from a polymer implant using ultrasound); J. Kost et al., *Proceed. Intern. Symp. Control. Rel. Bioact. Mater.* 16(141):294-295 (1989) (overview of the effect of ultrasound on the permeability of human skin and synthetic membranes); H. Benson et al., *Physical Therapy* 69(2):113-118 (1989) (effect of ultrasound on the percutaneous absorption of benzydamine); E. Novak, *Arch. Phys. Medicine & Rehab.* 45:231-232 (1964) (enhanced penetration of lidocaine through intact skin using ultrasound); J. E. Griffin et al., *Amer. J. Phys. Medicine* 44(1):20-25 (1965) (ultrasonic penetration of cortisol into pig tissue); J. E. Griffin et al., *J. Amer. Phys. Therapy Assoc.* 46:18-26 (1966) (overview of the use of ultrasonic energy in drug therapy); J. E. Griffin et al., *Phys. Therapy* 47(7):594-601 (1967) (ultrasonic penetration of hydrocortisone); J. E. Griffin et al., *Phys. Therapy* 48(12):1336-1344 (1968) (ultrasonic penetration of cortisol into pig tissue); J. E. Griffin et al., *Amer. J. Phys. Medicine* 51(2):62-72 (1972) (same); J. C. McElnay, *Int. J. Pharmaceutics* 40:105-110 (1987) (the effect of ultrasound on the percutaneous absorption of fluocinolone acetonide); and C. Escoffier et al., *Bioeng. Skin* 2:87-94 (1986) (in vitro study of the velocity of ultrasound in skin).

In addition to the aforementioned art, U.S. Pat. Nos. 4,767,402 and 4,780,212 to Kost et al. relate specifically to the use of specific frequencies of ultrasound to enhance the rate of permeation of a drug through human skin or through a synthetic membrane.

While the application of ultrasound in conjunction with drug delivery is thus known, results have for the most part been disappointing, i.e., enhancement of skin permeability has been relatively low.

SUMMARY OF THE INVENTION

The present invention provides a novel method for enhancing the rate of permeation of a given material through a selected intact area of an individual's body surface. The method comprises contacting the selected intact area with the material and applying ultrasound to the contacted area. The ultrasound preferably has a frequency of above about 10 MHz, and is continued at an intensity and for a period of time sufficient to enhance the rate of permeation of the material into and through the body surface. The ultrasound can also be used to pretreat the selected area of the body surface in preparation for drug delivery, or for diagnostic purposes, i.e., to enable non-invasive sampling of physiologic material beneath the skin or body surface.

In addition to enhancing the rate of permeation of a material, the present invention involves increasing the permeability of a biological membrane such as the stratum corneum by applying ultrasound having a frequency of above about 10 MHz to the membrane at an intensity and for a period of time sufficient to give rise to increased permeability of the membrane. Once the permeability of the membrane has been increased, it is possible to apply a material thereto and obtain an increased rate of flow of the material through the membrane.

It is accordingly a primary object of the invention to address the aforementioned deficiencies of the prior art by providing a method of enhancing the permeability of biological membranes and thus allow for an increased rate of delivery of material therethrough.

It is another object of the invention to provide such a method which is effective with or without chemical permeation enhancers.

It is still another object of the invention to minimize lag time in such a method and provide a relatively short total treatment time.

It is yet another object of the invention to provide such a method in which drug delivery is effected using ultrasound.

It is a further object of the invention to enable sampling of tissue beneath the skin or other body surface by application of high frequency (>10 MHz) ultrasound thereto.

A further feature of the invention is that it preferably involves ultrasound of a frequency greater than about 10 MHz.

Additional objects, advantages and novel features of the invention will be set forth in part in the description which follows, and in part will become apparent to those skilled in the art upon examination of the following, or may be learned by practice of the invention.

DETAILED DESCRIPTION OF PREFERRED EMBODIMENTS

Figure 1A:
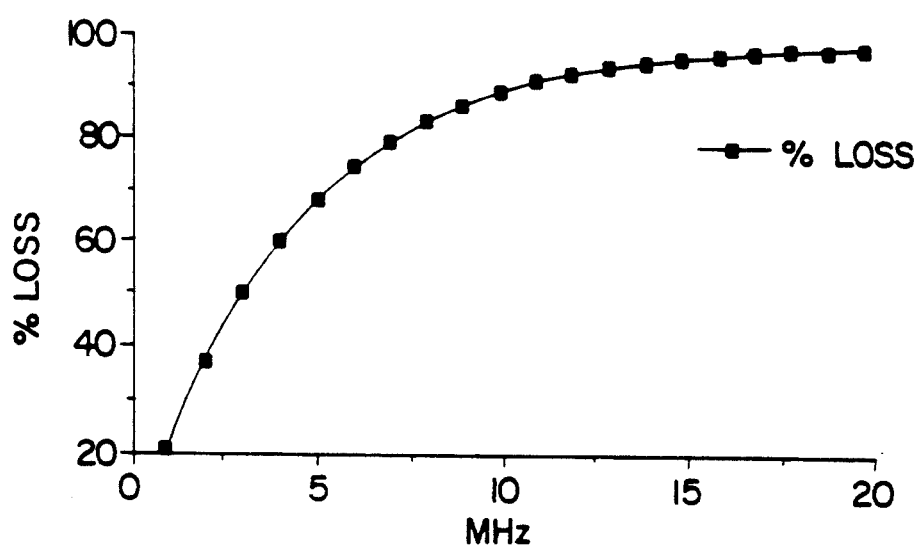
FIGS. 1A, 1B and 1C are theoretical plots of energy dissipation within the skin barrier versus frequency of applied ultrasound.

Before the present method of enhancing the rate of permeation of a material through a biological membrane and enhancing the permeability of membranes using ultrasound are disclosed and described, it is to be understood that this invention is not limited to the particular process steps and materials disclosed herein as such process steps and materials may, of course, vary. It is alto to be understood that the terminology used herein is used for purpose of describing particular embodiments only and is not intended to be limiting since the scope of the present invention will be limited only by the appended claims.

It must be noted that as used in this specification and the appended claims, the singular forms "a", "an" and "the" include plural reference unless the context clearly dictates otherwise. Thus, for example, reference to "a drug" includes mixtures of drugs and their pharmaceutically acceptable salts, reference to "an ultrasound device" includes one or more ultrasound devices of the type necessary for carrying out the present invention, and reference to "the method of administration" includes one or more different methods of administration known to those skilled in the art or which will become known to those skilled in the art upon reading this disclosure.

In one aspect of the invention a method is provided for enhancing the permeation of a given material such as a drug, pharmacologically active agent, or diagnostic agent into and/or through a biological membrane on an individual's body surface, which method comprises: (a) contacting the membrane with the chosen material in a pharmacologically acceptable carrier medium; and (b) applying ultrasound of an intensity and for a treatment time effective to produce delivery of the material through the membrane. The material is preferably a drug and it is preferable to obtain a desired blood level of the drug in the individual. The ultrasound is of a frequency and intensity effective to increase the permeability of the selected area to the applied drug over that which would be obtained without ultrasound. The ultrasound preferably has a frequency of more than 10 MHz, and may be applied either continuously or pulsed, preferably continuously. The ultrasound may be applied to the skin either before or after application of the drug medium so long as administration of the ultrasound and the drug medium is relatively simultaneous, i.e., the ultrasound is applied within about 6, more preferably within about 4, most preferably within about 2 minutes of drug application.

The invention is useful for achieving transdermal permeation of pharmacologically active agents which otherwise would be quite difficult to deliver through the skin or other body surface. For example, proteinaceous drugs and other high molecular weight pharmacologically active agents are ideal candidates for transdermal, transmucosal or topical delivery using the presently disclosed method. In an alternative embodiment, agents useful for diagnostic purposes may also be delivered into and/or through the body surface using the present method.

The invention is also useful as a non-invasive diagnostic technique, i.e., in enabling the sampling of physiologic material from beneath the skin or other body surface and into a collection (and/or evaluation) chamber.

The present invention will employ, unless otherwise indicated, conventional pharmaceutical methodology and more specifically conventional methodology used in connection with transdermal delivery of pharmaceutically active compounds and enhancers.

In describing the present invention, the following terminology will be used in accordance with the definitions set out below.

A "biological membrane" is intended to mean a membrane material present within a living organism which separates one area of the organism from another and, more specifically, which separates the organism from its outer environment. Skin and mucous membranes are thus included.

"Penetration enhancement" or "permeation enhancement" as used herein relates to an increase in the permeability of skin to a material such as a pharmacologically active agent, i.e., so as to increase the rate at which the material permeates into and through the skin. The present invention involves enhancement of permeation through the use of ultrasound, and, in particular, through the use of ultrasound having a frequency of greater than 10 MHz.

"Transdermal" (or "percutaneous") shall mean passage of a material into and through the skin to achieve effective therapeutic blood levels or deep tissue therapeutic levels. While the invention is described herein primarily in terms of "transdermal" administration, it will be appreciated by those skilled in the art that the presently disclosed and claimed method also encompasses the "transmucosal" and "topical" administration of drugs using ultrasound. "Transmucosal" is intended to mean passage of any given material through a mucosal membrane of a living organism and more specifically shall refer to the passage of a material from the outside environment of the organism, through a mucous membrane and into the organism. "Transmucosal" administration thus includes delivery of drugs through either nasal or buccal tissue. By "topical" administration is meant local administration of a topical pharmacologically active agent to the skin as in, for example, the treatment of various skin disorders or the administration of a local anaesthetic. "Topical" delivery can involve penetration of a drug into the skin but not through it, i.e., topical administration does not involve actual passage of a drug into the bloodstream.

"Carriers" or "vehicles" as used herein refer to carrier materials without pharmacological activity which are suitable for administration with other pharmaceutically active materials, and include any such materials known in the art, e.g., any liquid, gel, solvent, liquid diluent, solubilizer, or the like, which is nontoxic and which does not interact with the drug to be administered in a deleterious manner. Examples of suitable carriers for use herein include water, mineral oil, silicone, inorganic gels, aqueous emulsions, liquid sugars, waxes, petroleum jelly, and a variety of other oils and polymeric materials.

By the term "pharmacologically active agent" or "drug" as used herein is meant any chemical material or compound suitable for transdermal or transmucosal administration which can either (1) have a prophylactic effect on the organism and prevent an undesired biological effect such as preventing an infection, (2) alleviates a condition caused by a disease such as alleviating pain caused as a result of a disease, or (3) either alleviates or completely eliminates the disease from the organism. The effect of the agent may be local, such as providing for a local anaesthetic effect or it may be systemic. Such substances include the broad classes of compounds normally delivered through body surfaces and membranes, including skin. In general, this includes: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionzed drugs may be delivered, as can drugs of either high or low molecular weight.

Proteinaceous and polypeptide drugs represent a preferred class of drugs for use in conjunction with the presently disclosed and claimed invention. Such drugs cannot generally be administered orally in that they Are often destroyed in the G.I. tract or metabolized in the liver. Further, due to the high molecular weight of most polypeptide drugs, conventional transdermal delivery systems are not generally effective. It is also desirable to use the method of the invention in conjunction with drugs to which the permeability of the skin is relatively low, or which give rise to a long lag-time (application of ultrasound as described herein has been found to significantly reduce the lag-time involved with the transdermal administration of most drugs).

By a "therapeutically effective" amount of a pharmacologically active agent is meant a nontoxic but sufficient amount of a compound to provide the desired therapeutic effect. The desired therapeutic effect may be a prophylactic effect, in preventing a disease, an effect which alleviates a system of the disease, or a curative effect which either eliminates or aids in the elimination of the disease.

As noted above, the present invention is a method for enhancing the rate of permeation of a drug through an intact area of an individual's body surface, preferably the human skin. The method involves transdermal administration of a selected drug in conjunction with ultrasound. Ultrasound causes thermal, mechanical and chemical alterations of biological tissue, thereby enhancing the rate of permeation of a given material therethrough.

While not wishing to be bound by theory, applicants propose that the use of higher frequency ultrasound as disclosed herein specifically enhances the permeation of the drug through the outer layer of skin, i.e., the stratum corneum, by causing momentary and reversible perturbations within (and thus short-term, reversible reduction in the barrier function of) the layer of the stratum corneum. It will be appreciated by those skilled in the art of transdermal drug delivery that a number of factors related to the present method will vary with the drug to be administered, the disease or injury to be treated, the age of the selected individual, the location of the skin to which the drug is applied, and the like.

As noted above, "ultrasound" is ultrasonic radiation of a frequency above 20,000 Hz. As may be deduced from the literature cited above, ultrasound used for most medical purposes typically employs frequencies ranging from 1.6 to about 10 MHz. The present invention, by contrast, employs ultrasound frequencies of greater than about 10 MHz, preferably in the range of about 15 to 50 MHz, most preferably in the range of about 15 to 25 MHz. It should be emphasized that these ranges are intended to be merely illustrative of the preferred embodiment; in some cases higher or lower frequencies may be used.

The ultrasound may be pulsed or continuous, but is preferably continuous when lower frequencies are used. At very high frequencies, pulsed application will generally be preferred so as to enable dissipation of generated heat.

The preferred intensity of the applied ultrasound is less than about 5.0 W/cm$^2$, more preferably is in the range of about 0.01 to 5.0 W/cm$^2$, and most preferably is in the range of 0.05 to 3.0 W/cm$^2$. The total treatment time, i.e., the period over which drug and ultrasound are administered, will vary depending on the drug administered, the disease or injury treated, etc., but will generally be on the order of about 30 seconds to 60 minutes, preferably 5 to 45 minutes, more preferably 5 to 30 minutes, and most preferably 5 to 10 minutes. It should be noted that the aforementioned ranges represent suggested, or preferred, treatment times, but are not in any way intended to be limiting. Longer or shorter times may be possible and in some cases desirable. Virtually any type of device may be used to administer the ultrasound, providing that the device is callable of producing the higher frequency ultrasonic waves required by the present method. A device will typically have a power source such as a small battery, a transducer, a reservoir in which the drug medium is housed (and which may or may not be refillable), and a means to attach the system to the desired skin site.

As ultrasound does not transmit well in air, a liquid medium is generally needed to efficiently and rapidly transmit ultrasound between the ultrasound applicator and the skin. As explained by P. Tyle et al., cited above, the selected drug medium should contain a "coupling" or "contacting" agent typically used in conjunction with ultrasound. The coupling agent should have an absorption coefficient similar to that of water, and furthermore be nonstaining, nonirritating to the skin, and slow drying. It is clearly preferred that the coupling agent retain a paste or gel consistency during the time period of ultrasound administration so that contact is maintained between the ultrasound source and the skin. Examples of preferred coupling agents are mixtures of mineral oil and glycerine and propylene glycol, oil/water emulsions, and a water-based gel. A solid-state, noncrystalline polymeric film having the above-mentioned characteristics may also be used. The drug medium may also contain a carrier or vehicle, as defined alone.

A transdermal patch as well known in the art may be used in conjunction with the present invention, i.e., to deliver the drug medium to the skin. The "patch", however, must have the properties of the coupling agent as described in the preceding paragraph so as to enable transmission of the ultrasound from the applicator, through the patch, to the skin.

As noted earlier in this section, virtually any chemical material or compound suitable for transdermal, transmucosal or topical administration may be administered using the present method. Again, the present invention is particularly useful to enhance delivery of proteinaceous and other high molecular weight drugs.

The method of the invention is preferably carried out as follows. The drug medium, i.e., containing the selected drug or drugs in conjunction with the coupling agent and optionally a carrier or vehicle material, is applied to an area of intact body surface. Ultrasound preferably having a frequency greater than about 10 MHz may be applied before or after application of the drug medium, but is preferably applied immediately before application of the drug so as to "pretreat" the skin prior to drug administration.

It should also be pointed out that the present method may be used in conjunction with a chemical permeation enhancer as known in the art, wherein the ultrasound enables the use of much lower concentrations of permeation enhancer—thus minimizing skin irritation and other problems frequently associated with such compounds—than would be possible in the absence of ultrasound. The permeation enhancer may be incorporated into the drug medium or it may be applied in a conventional transdermal patch after pretreatment of the body surface with ultrasound.

The present invention may also be used in conjunction with iontophoresis for drugs which are particularly difficult to administer through the skin, i.e., because of the low permeability of the stratum corneum to such drugs. The selected area of the body surface is pretreated with ultrasound and the drug is then administered using conventional iontophoresis techniques.

With respect to skin location, virtually any area of the body surface may be selected so long as it is intact, however, the thickness and permeability of skin at the site of exposure will affect the treatment conditions, i.e., intensity, frequency, contact time, exposure time, and the like. The area of skin through which the drug medium and the ultrasound will be administered can again vary greatly, but will typically be on the order of 1 to 100 cm$^2$, more typically on the order of 50 to 100 cm$^2$, most typically on the order of 10 to 50 cm$^2$.

EXAMPLE

Figure 1B:
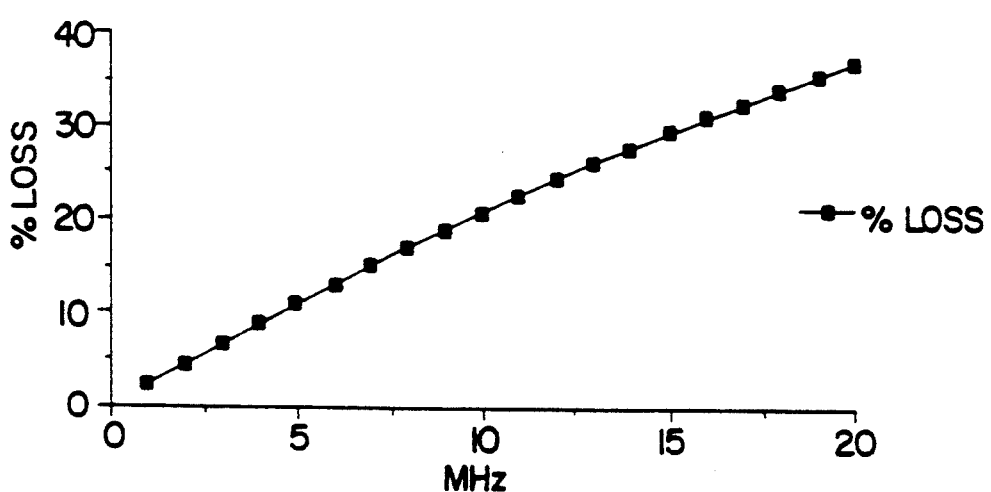
Figure 1C:
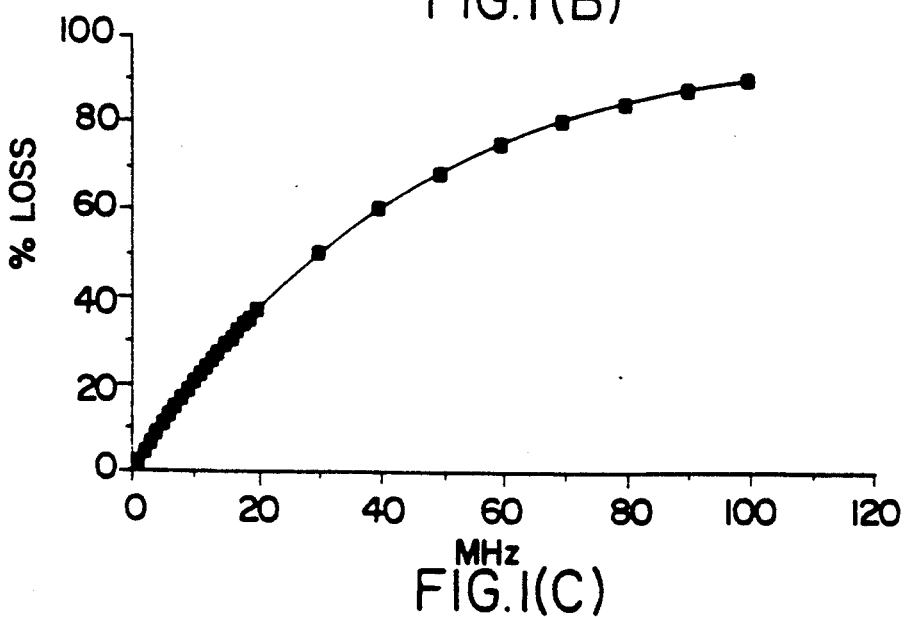

Based on the present inventors' theoretical analysis of the propagation of ultrasound energy in tissue and the barrier properties of skin, it was concluded that higher ultrasound frequencies might be more effective in enhancing the flux of drug molecules across the skin. This conclusion, based on the assumption that enhancement is proportional to the amount of energy dissipation within the barrier, is supported by FIG. 1, which suggests that, within the first millimeter of skin, ultrasound energy dissipation increases exponentially with frequency.

To test the hypothesis that higher frequencies (>10 MHz) would yield greater enhancement, in vivo experiments were performed on hairless guinea pigs. The setup for carrying out the experiment consisted of a function generator, transducers tuned at different frequencies and a power-meter. $^{14}$C-labeled salicylic acid was used as the "model" marker drug molecule. A saturated solution of unlabeled salicylic acid in water was prepared. Carbopol TM (B.F. Goodrich), a polymer, was added to this solution to make a gel containing salicylic acid at a concentration of 0.57% w/w. This gel was then spiked with a known amount of radiolabeled salicylic acid (approx. 2.27 µCi/mg gel). Approximately 30 mg gel per square centimeter of transducer cross-sectional area was then applied to the skin surface of the guinea pigs' flanks. This gel served as both the drug reservoir and the coupling medium between the transducer and skin surface. Frequencies of 1, 7.5 and 16 MHz were tested using an intensity of 0.25 W/cm$^2$ and treatment periods (time of exposure of the skin to both drug and ultrasound) of 10 and 20 minutes. At the treatment site, the transducer delivered ultrasound at the appropriate frequency for the designated period. At the control site, in the contralateral flank, the transducer was positioned on the skin, but not activated. Thus, each animal served as its own control.

Enhancement was quantified in two ways: (1) by tape-stripping the outer skin layer at the treatment and control sites immediately after the experimental period (radioactivity in the tape strips was then determined by liquid scintillation counting); and (2) by measuring the cumulative amount of $^{14}C$ excreted in the animals' urine up to 14 hours after initiation of the experiment.

Figure 2:
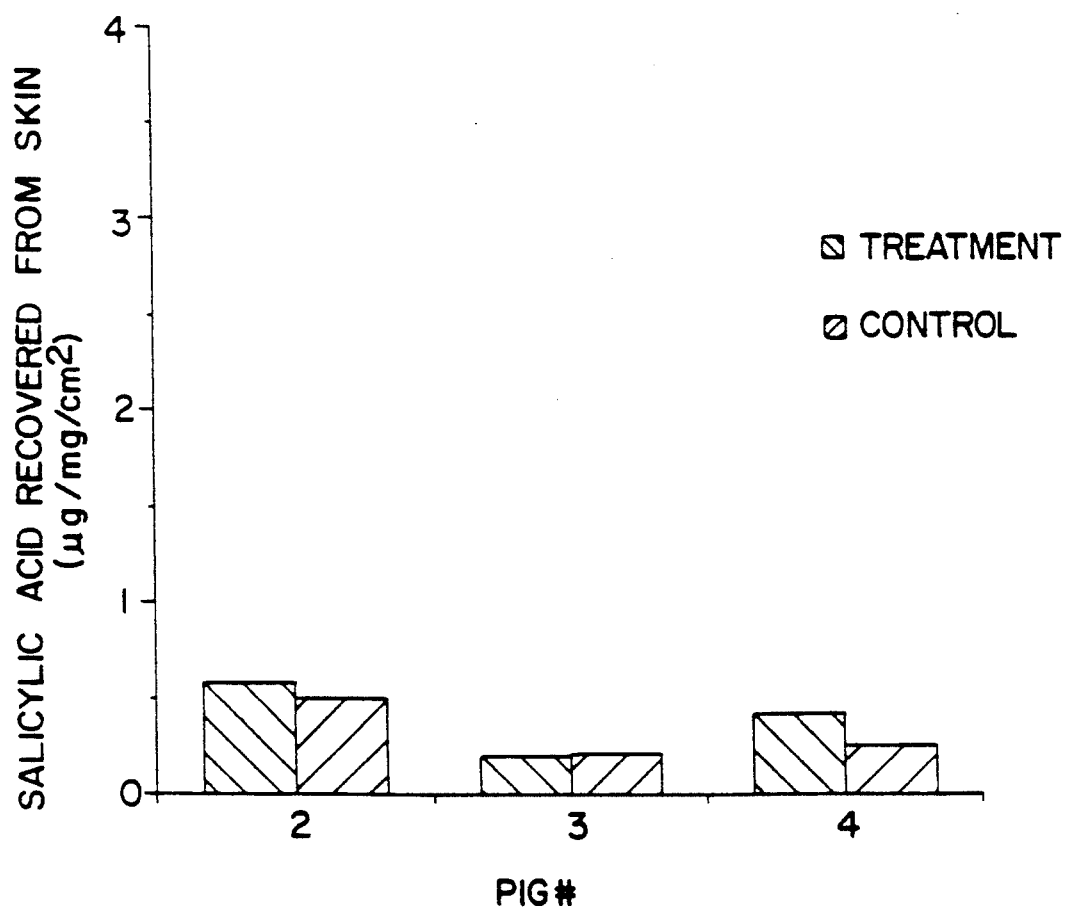
FIGS. 2, 3 and 4 are graphic representations of the amount of salicylic acid recovered from the stratum corneum after ultrasound treatment at different frequencies.
Figure 3:
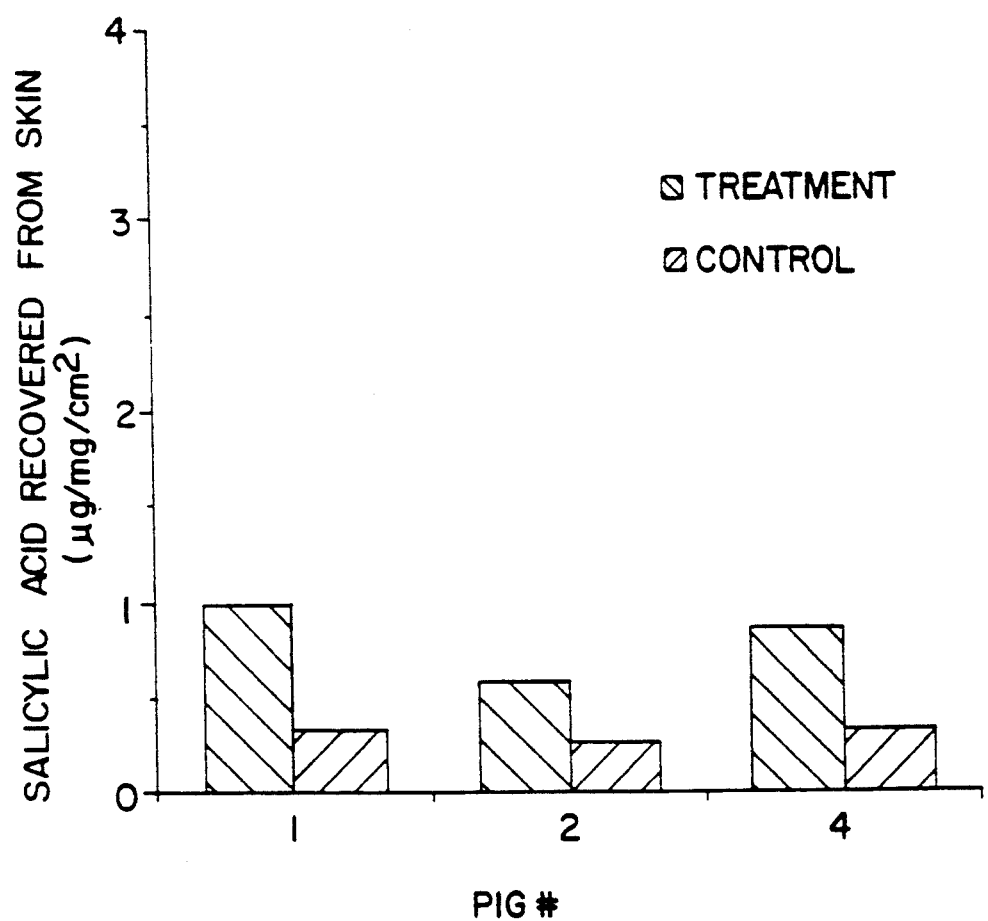
Figure 4:
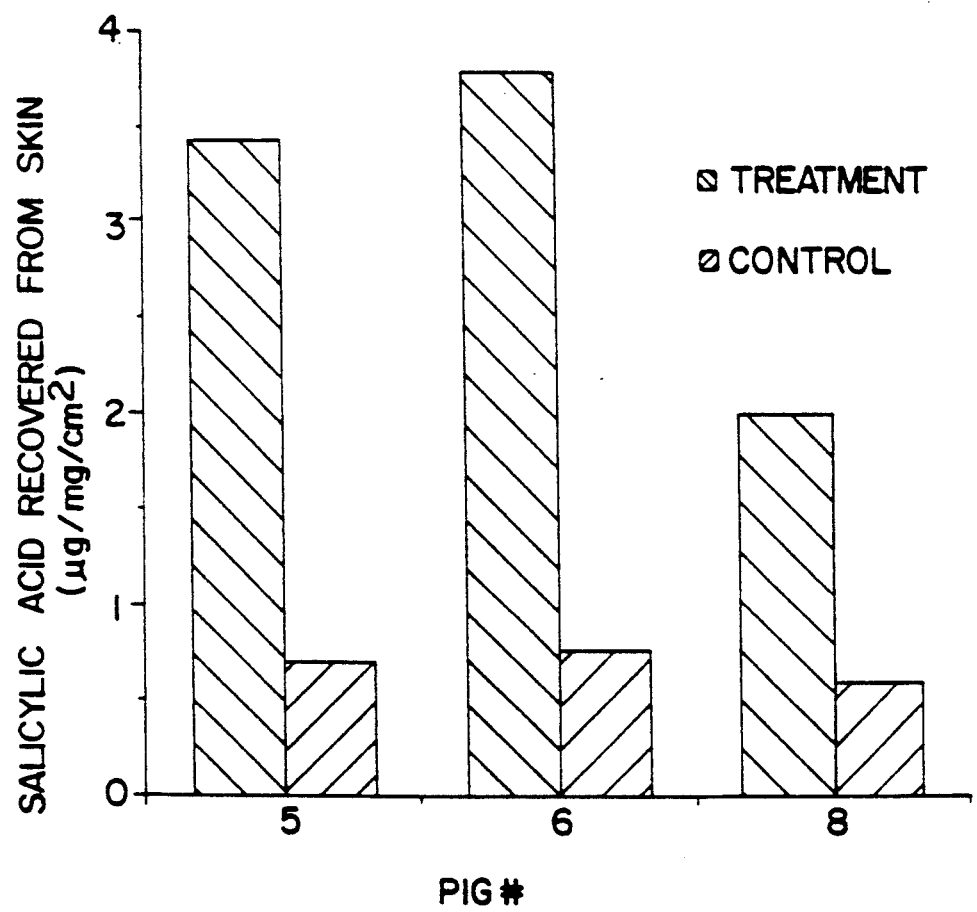
Figure 5:
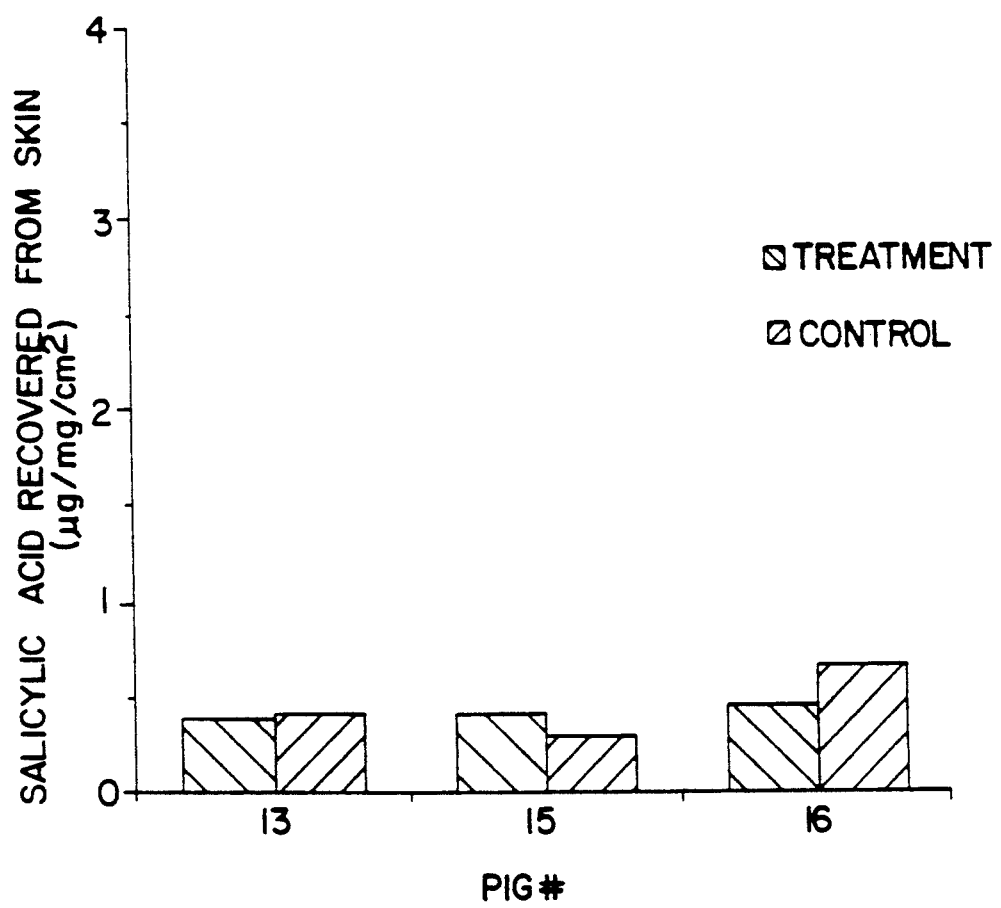
FIGS. 5 and 6 represent the results of experiments similar to those summarized in FIGS. 2, 3 and 4, but with a shorter treatment time.
Figure 6:
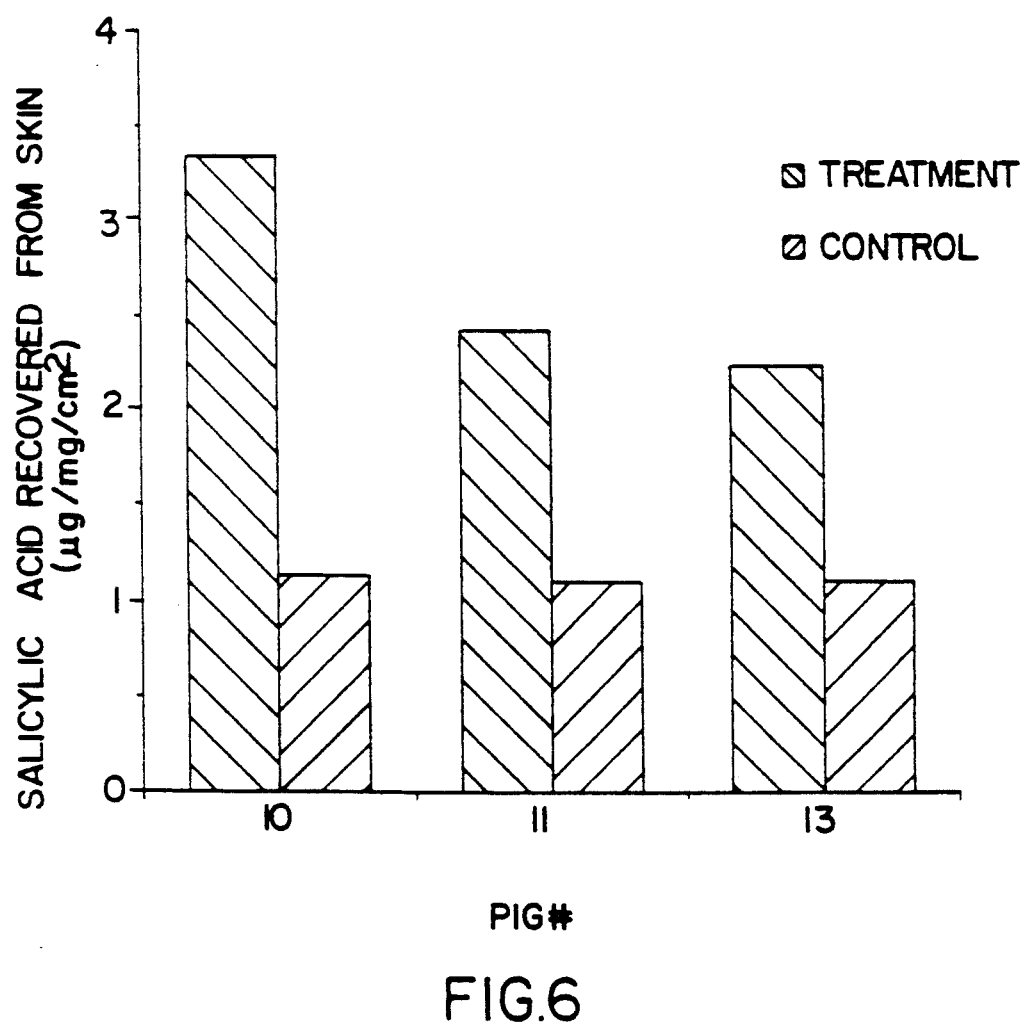
Figure 7:
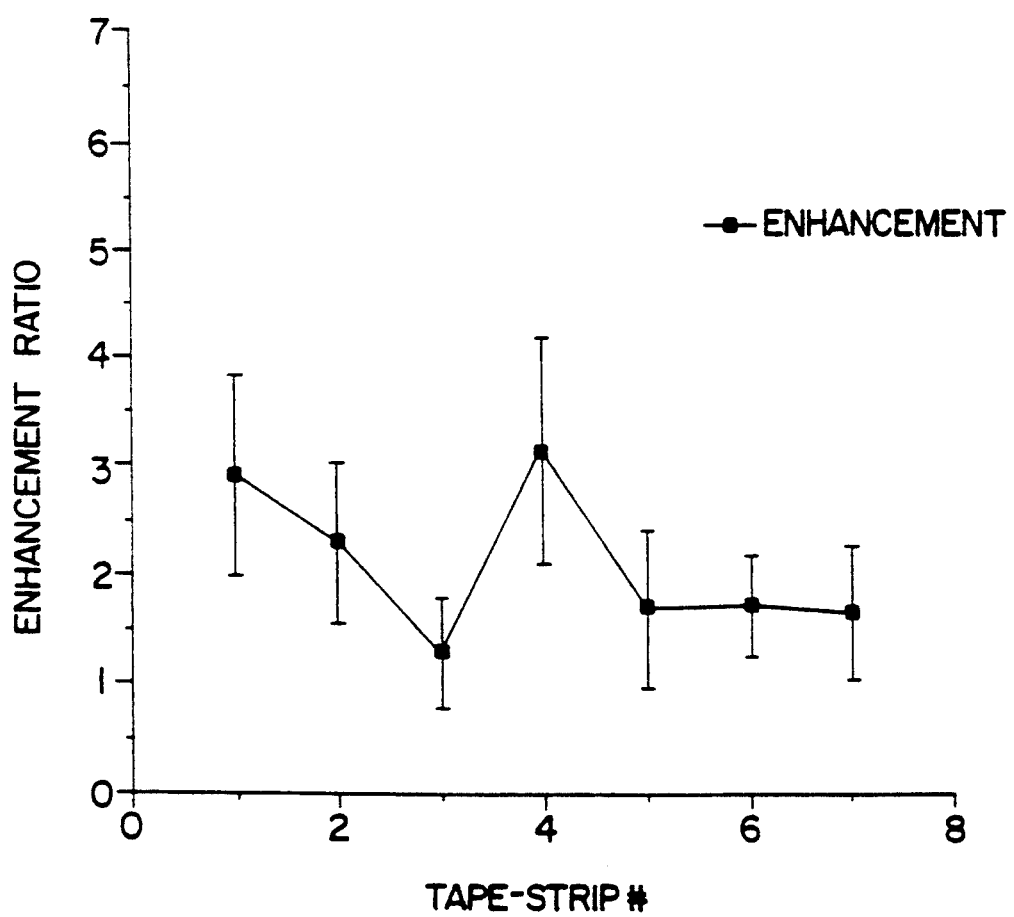
FIGS. 7, 8, 9 and 10 are plots of enhancement versus "tape-strip number," as described in the Example.
Figure 8:
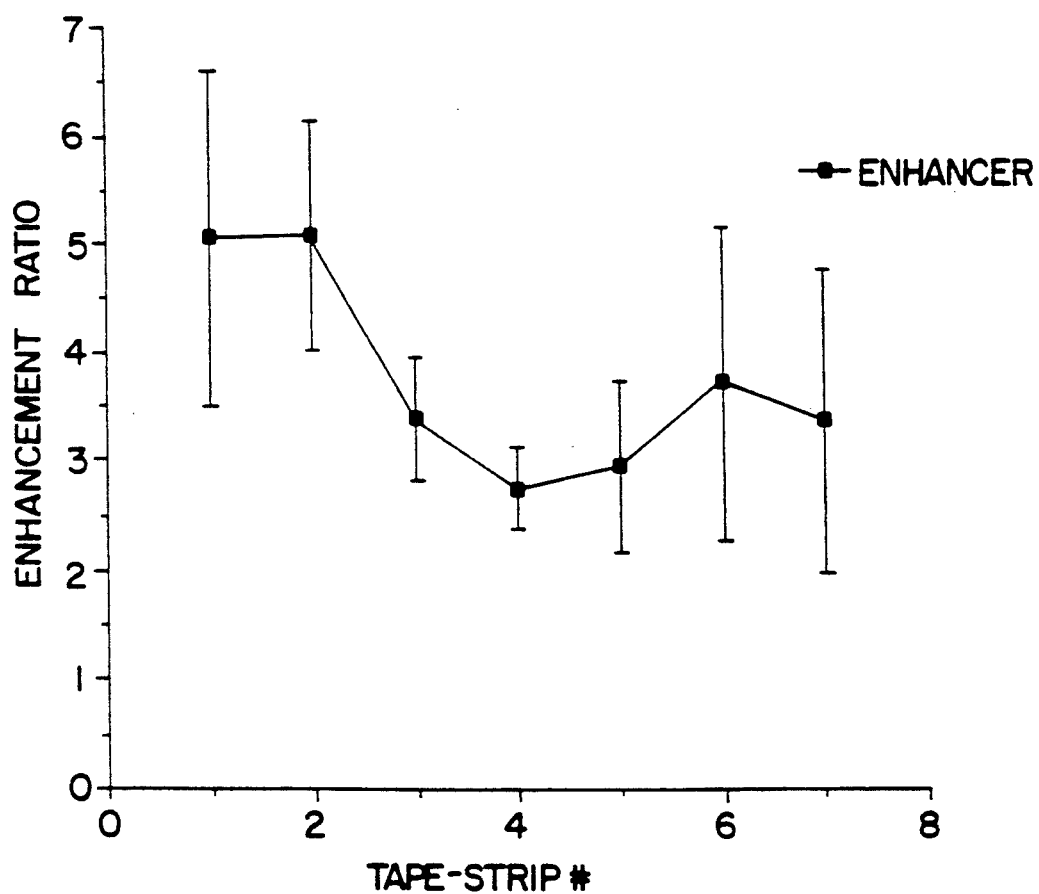
Figure 9:
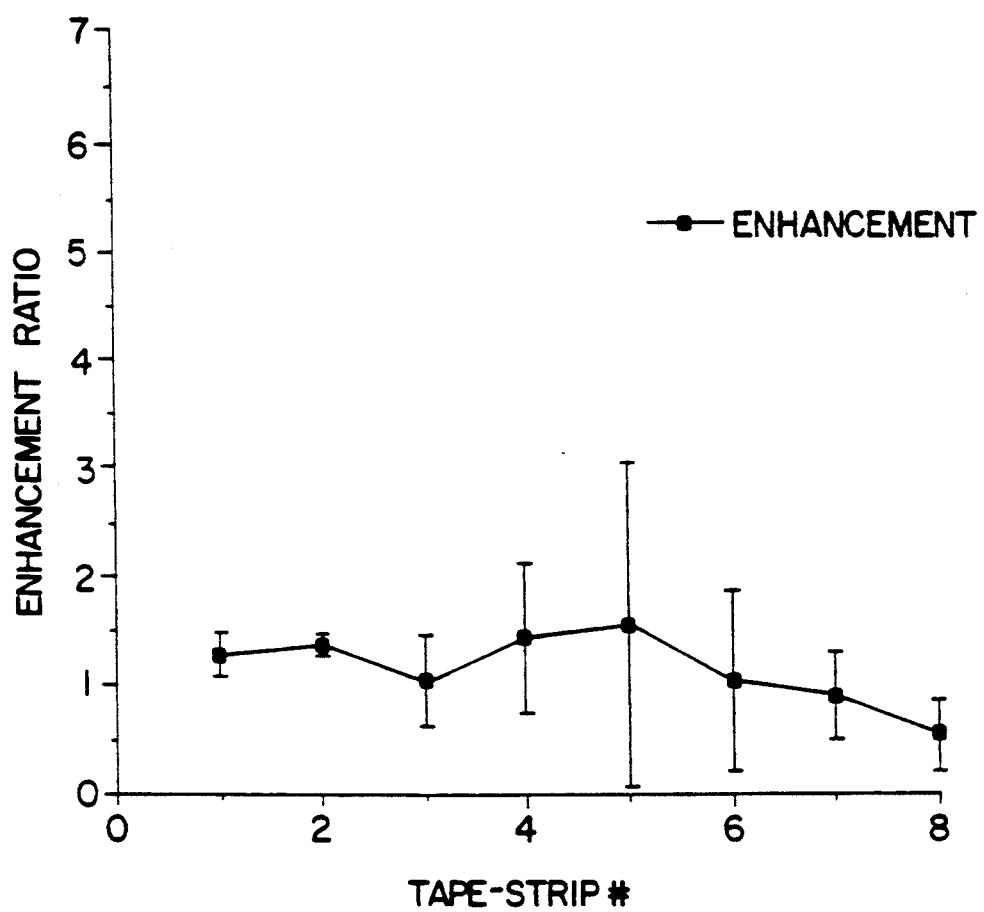
Figure 10:
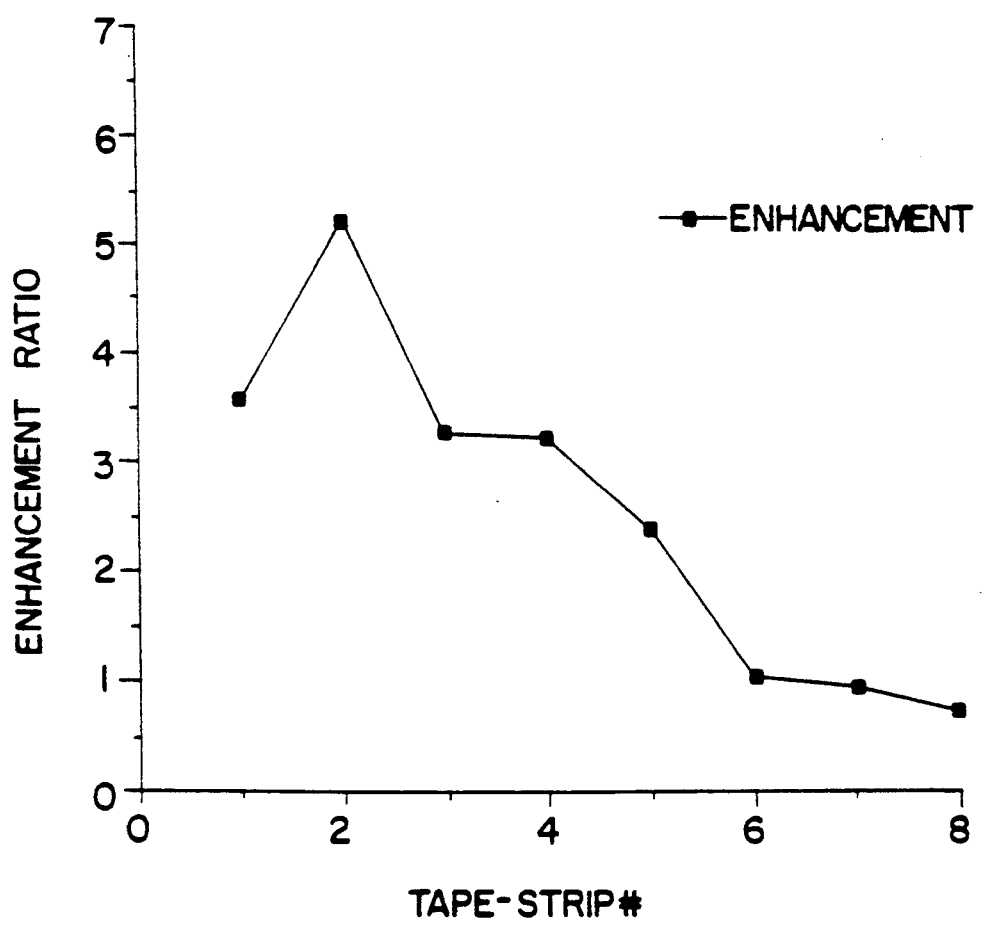

(1) Tape-strip procedure: It has been established that the uppermost layer of skin, the stratum corneum (SC), offers the most resistance to drug penetration. Hence, it was decided to compare the amount of radioactivity present in the SC after ultrasound treatment with that after the control experiment (passive diffusion, no ultrasound). FIGS. 2, 3 and 4 present a comparison of the total amount of salicylic acid that had penetrated into the SC with 1, 7.5 and 16 MHz exposure for 20 minutes and without exposure to ultrasound. As can be seen, use of 16 MHz resulted in a significantly elevated drug level in the SC as compared to the control. FIGS. 5 and 6 are comparable to FIGS. 3 and 4, but here the treatment time was 10 minutes, rather than 20 minutes. Each tape strip removed a certain amount of the SC. Hence, with increasing tape-strip number, tissue further away from the surface was examined. Therefore, a plot of the amount of drug in each strip against strip number reflects the concentration gradient of drug in the SC. Such plots are shown in FIGS. 7, 8, 9 and 10. The ordinate is the ratio of the amount of radioactivity in the tape-strip after treatment to the amount in the strip after control.

Figure 11:
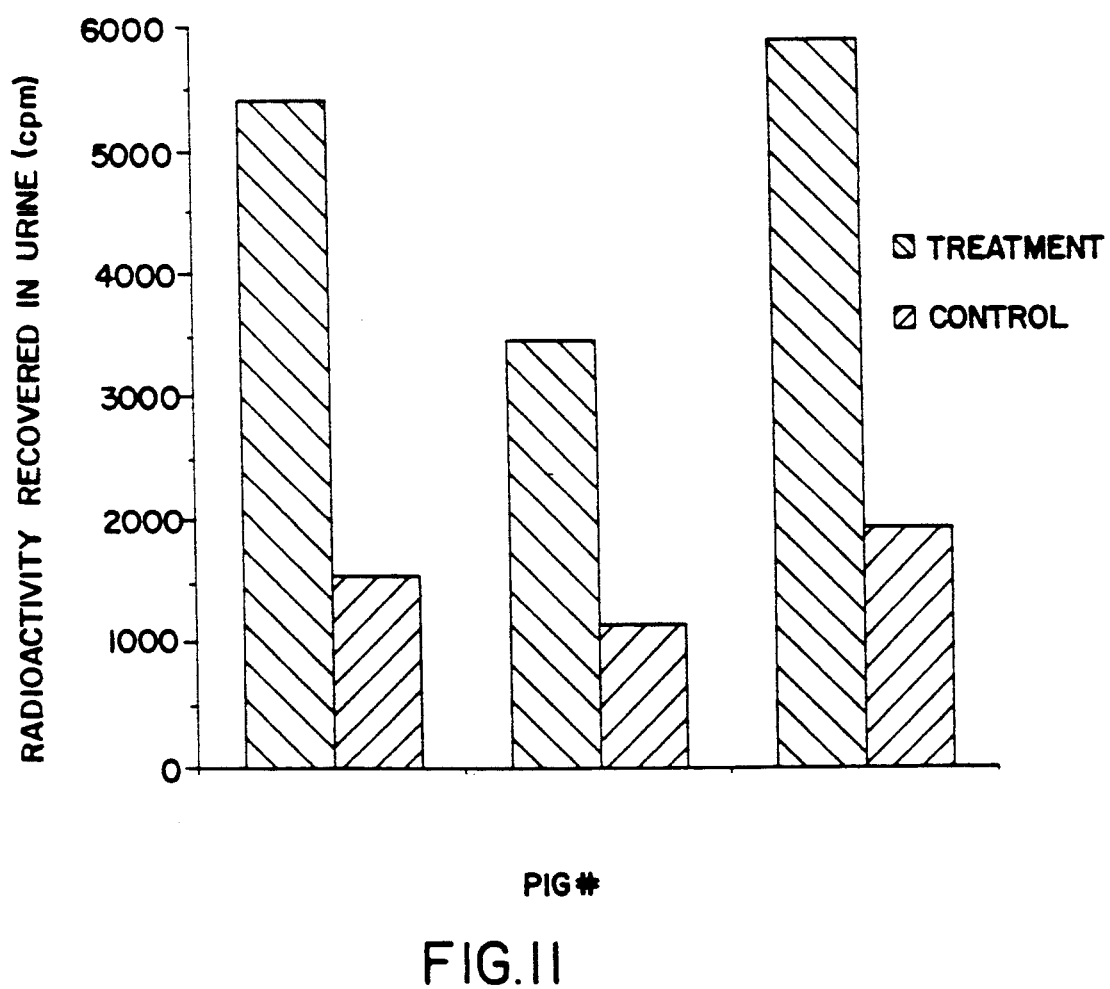
FIG. 11 illustrates the effect of ultrasound on the systemic availability of salicylic acid following topical application.

(2) Urinary excretion: To confirm that the amount of drug recovered from the SC reflected the amount of drug penetrated, radioactivity excreted in the urine was monitored. FIG. 11 graphically illustrates a comparison of the total amount of radioactivity excreted in urine 14 hours after a 20 minute treatment using 16 MHz and the corresponding control. At least five times more drug entered the systemic circulation with ultrasound than without.

While the present invention has been described with reference to specific embodiments thereof, it should be understood by those skilled in the art that various changes may be made and equivalents may be substituted without departing from the true spirit of the scope of the invention. In addition, many modifications may be made to adapt a particular ultrasound device, drug, excipient material, process, process step or steps, to the objective, spirit and scope of the present invention. All such modifications are intended to be within the scope of the claims appended hereto.

We claim:

1. A method for enhancing the rate of permeation of a drug medium into a selected intact area of an individual's body surface, which method comprises:
    (a) applying ultrasound having a frequency of above 10 MHz to said selected area, at an intensity and for a period of time effective to enhance the permeability of said selected area;
    (b) contacting the selected area with the drug medium; and
    (c) effecting passage of said drug medium into and through said selected area by means of iontophoresis.

2. The method of claim 1, wherein said ultrasound frequency is in the range of about 15 MHz to 50 MHz.

3. The method of claim 2, wherein said ultrasound frequency is in the range of about 15 to 25 MHz.

4. The method of claim 1, wherein said period of time is in the range of about 5 to 45 minutes.

5. The method of claim 4, wherein said period of time is in the range of about 5 to 30 minutes.

6. The method of claim 1, wherein said period of time is less than about 10 minutes.

7. The method of claim 1, wherein said intensity of said ultrasound is less than about 5.0 W/cm$^2$.

8. The method of claim 7, wherein said intensity of said ultrasound is in the range of about 0.01 to 5.0 W/cm$^2$.

9. The method of claim 8, wherein said intensity of said ultrasound is in the range of about 0.05 to 3.0 W/cm$^2$.

10. The method of claim 1, wherein said area of the stratum corneum is in the range of about 1 to 100 cm$^2$.

11. The method of claim 10, wherein said area of the stratum corneum is in the range of about 5 to 100 cm$^2$.

12. The method of claim 11, wherein said area of the stratum corneum is in the range of about 10 to 50 cm$^2$.

13. The method of claim 1 wherein said drug medium comprises a drug and a coupling agent effective to transfer said ultrasound to the body from an ultrasound source.

14. The method of claim 13 wherein said coupling agent is a polymer or a gel.

15. The method of claim 13 wherein said coupling agent is selected from the group consisting of glycerin, water, and propylene glycol.

16. The method of claim 1 wherein said drug medium further comprises a chemical permeation enhancer.

17. The method of claim 1, wherein steps (a) and (b) are carried out approximately simultaneously.

18. The method of claim 1, wherein step (b) is carried out before step (a).

19. The method of claim 1, wherein step (a) is carried out before step (b).

20. The method of claim 1, wherein the ultrasound is applied continuously.

21. The method of claim 1, wherein the ultrasound is pulsed.

* * * * *